(12) United States Patent
Martin et al.

(10) Patent No.: US 6,194,769 B1
(45) Date of Patent: Feb. 27, 2001

(54) SENSOR DEVICES COMPRISING FIELD-STRUCTURED COMPOSITES

(75) Inventors: James E. Martin, Tijeras; Robert C. Hughes; Robert A. Anderson, both of Albuquerque, all of NM (US)

(73) Assignee: Sandia Corporation, Albuquerque, NM (US)

( * ) Notice: Subject to any disclaimer, the term of this patent is extended or adjusted under 35 U.S.C. 154(b) by 0 days.

(21) Appl. No.: 09/323,172

(22) Filed: May 27, 1999

(51) Int. Cl.[7] .......................... H01L 27/14; H01L 29/82; H01L 29/84
(52) U.S. Cl. .......................... 257/414; 257/428; 257/417
(58) Field of Search .......................... 257/414, 421, 257/428, 48, 467, 429, 417; 324/390, 401, 391

(56) References Cited

U.S. PATENT DOCUMENTS

| | | | |
|---|---|---|---|
| 4,020,830 | * | 5/1977 | Johnson et al. . |
| 4,058,368 | * | 11/1977 | Svensson et al. . |
| 5,378,995 | * | 1/1995 | Kudo et al. . |
| 5,574,377 | * | 11/1996 | Marquez-Lucero et al. . |
| 6,010,616 | * | 1/2000 | Lewis et al. . |
| 6,017,440 | * | 1/2000 | Lewis et al. . |

* cited by examiner

*Primary Examiner*—Sheila V. Clark
(74) *Attorney, Agent, or Firm*—Brian M. Dodson (57) ABSTRACT

A new class of sensor devices comprising field-structured conducting composites comprising a textured distribution of conducting magnetic particles is disclosed. The conducting properties of such field-structured materials can be precisely controlled during fabrication so as to exhibit a large change in electrical conductivity when subject to any environmental influence which changes the relative volume fraction. Influences which can be so detected include stress, strain, shear, temperature change, humidity, magnetic field, electromagnetic radiation, and the presence or absence of certain chemicals. This behavior can be made the basis for a wide variety of sensor devices.

25 Claims, 6 Drawing Sheets

SENSOR DEVICES COMPRISING FIELD-STRUCTURED COMPOSITES

This invention was made with Government support under Contract DE-AC04-94DP85000 awarded by the U.S. Department of Energy. The Government has certain rights in the invention.

BACKGROUND

The present invention relates to a new class of environmental sensors based on the properties of field structured composites. Such composites possess a substructure of ordered aggregates of suspended conducting magnetic particles. This substructure self-assembles under the influence of an external magnetic field, and induces a wide range of mechanical, dielectric, magnetic, and optical properties which can be harnessed to make sensors. These new materials enable a broad range of sensor devices and other applications.

The conduction of electricity in materials comprising a particulate conducting phase dispersed in a nonconducting medium have been of scientific and practical interest for some time. Such materials as conductive inks, some forms of conducting polymers, and static elimination materials have long used such dispersions to provide conductivity to conventionally non-conducting elements.

Such composites have been formed of a composite mixture of conducting particles essentially uniformly distributed in a nonconducting medium. Roughly speaking, one expects the conductivity of a composite mixture to increase as the volume fraction of the dispersed conducting phase increases (i.e., as more conductive particles are introduced into the mixture). This is true, but the bulk conductivity of the composite is not simply proportional to the volume fraction of the dispersed phase. In fact, there is a rather well defined point at which long-range conducting paths appear, called the critical volume fraction.

Near the critical volume fraction, there are many conducting paths that are only interrupted by a few instances where current conduction must go through particles which are nearly, but not quite in contact. Small changes in the particle volume fraction can complete many of the paths, making the conductivity of these materials very sensitive to such changes.

A typical prior art sensor based on such essentially uniform composite materials appears in U.S. Pat. No. 5,574,377. Here a chemical sensor is implemented by measuring the electrical resistance of a composite material formed of a gel-like polymer containing dispersed conducting particles with volume fraction near the critical volume fraction. The sensor material has large conductivity in the absence of external chemicals. However, the sensor material (more particularly the nonconducting polymer) swells when in the presence of certain organic solvents. Such swelling increases the gaps between particles, thereby driving a large reduction in the bulk conductivity of the sensor material. Such chemical sensors can be quite sensitive if the proper volume fraction is achieved in the sensor material.

Despite the clear potential for using such conducting composite materials for a variety of sensor functions, practical applications have been limited by prior art fabrication technology. It is very difficult to disperse conducting particles uniformly in a nonconducting medium. Exceedingly small changes in process conditions, or simply random variations in the local volume fraction of the conducting particles, can reduce or destroy the desired material response.

Thus, conducting composite materials made using conventional technology cannot be routinely applied to most sensor applications unless a great deal of effort is taken to control and then characterize the composite. Numerous samples must be typically made under slightly varying conditions, and the samples then individually characterized in a search for individual pieces having the proper bulk properties. When such composites can be used, the device or mechanism thereby enabled usually requires individual calibration.

There is thus a longstanding need for sensor devices which exhibit the special properties of composite materials comprising conducting particles, but which can be reliably manufactured to exhibit precise and predefined device properties.

The present invention addresses the aforementioned need by substituting for prior art conducting composite materials a new class of conducting composite materials, called field-structured composites (FSC) in which the suspended conducting magnetic particles form an ordered aggregate structure within the nonconducting medium. This structure can be controlled during fabrication to yield a precise and predetermined composite structure, avoiding the prior art fabrication difficulties.

Figure 1A:
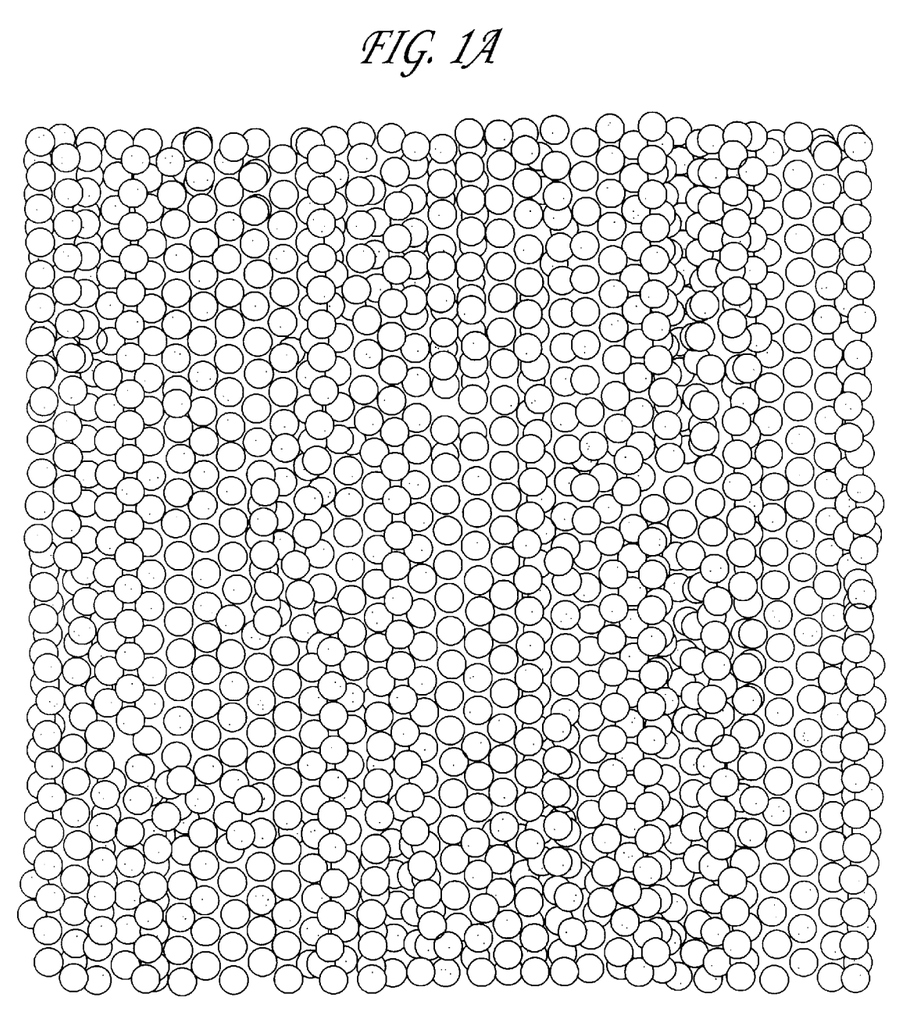
FIG. 1a shows a field-structured material comprising rod-like aggregate structures.
Figure 1B:
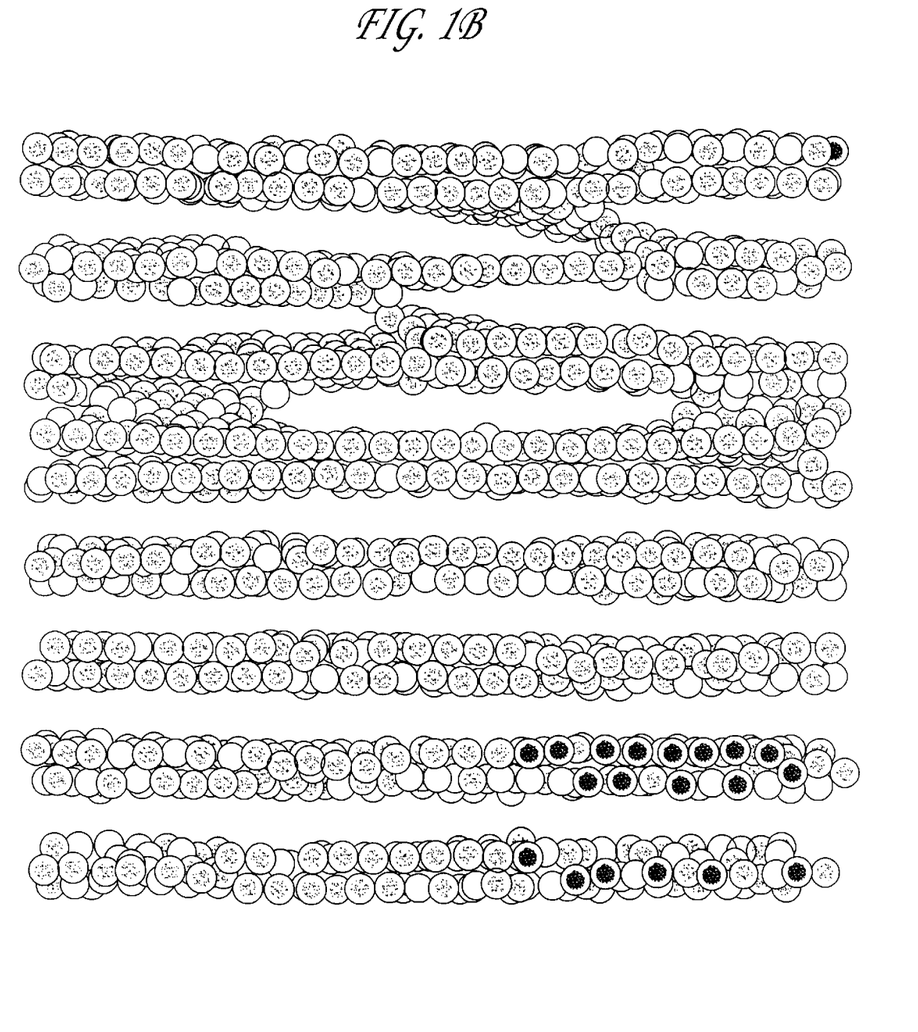
FIG. 1b shows a field-structured material comprising sheet-like aggregate structures.

Such a field-structured composite can be made beginning with a nominally uniform dispersion of magnetic particles in a nonconducting fluid that can be solidified. This initial dispersion is typically chosen to have a volume fraction well below the critical volume fraction for a uniform distribution. To form a uniaxial field-structured composite, an external magnetic field of fixed orientation is applied to this initial dispersion. This magnetic field aligns the particles into thin rod-like aggregations of particles which form an interconnecting network within the fluid (see FIG. 1a). This network of particles will conduct, even though the sample is beneath the critical volume fraction for a uniformly dispersed material. Conduction perpendicular to the rods is enabled by the presence of conducting bridges between rods.

A distinct type of FSC can be fabricated by rotating the initial dispersion within the magnetic field around an axis perpendicular to the magnetic field direction. In this case, the particles aggregate into thin sheets of closely packed particles, with relatively few interconnections between these sheets. Both the rod-like aggregations and the sheet-like aggregations are examples of ordered aggregate structures.

The ordered aggregate structure of an FSC can be precisely controlled during fabrication by controlling the process parameters. These process parameters include the time the dispersion is subjected to the structuring magnetic field, the strength of the magnetic field, and the direction of the magnetic field as a function of time. When the desired ordered aggregate structure has been attained, the fluid can be solidified (e.g., by freezing or polymerizing).

Beyond such issues of fabrication control, however, the basic nature of the transition between the nonconducting and the conducting states in a field-structured composite is fundamentally distinct from that in a uniform dispersion of conducting particles. This is a result of the highly anisotropic local structure in field-structured composites. Control over this structure can allow fabrication of composites in which the average bulk conducting path is interrupted by fewer weak conducting links between particles than is found in uniform dispersions. Such structures are dramatically more sensitive than are uniform dispersions in the type of sensor applications included in the present invention.

SUMMARY

The present application is directed to a new class of sensor devices comprising field-structured conducting composites comprising conducting magnetic particles. The microstructure and conducting properties of such field-structured composites can be precisely controlled during fabrication. Such materials show a large change in electrical conductivity when subject to a large number of environmental influences, including stress, strain, shear, acceleration, temperature change, light, and the presence or absence of certain chemicals. This behavior enables the wide variety of sensor devices described herein.

BRIEF DESCRIPTION OF THE ILLUSTRATIONS

FIG. 1 shows a schematic illustration of two canonical types of field-structured materials.

FIG. 3 shows schematic illustrations of field-structured stress sensors.

FIG. 4 shows schematic illustrations of field-structured acceleration sensors.

DETAILED DESCRIPTION

The field-structured devices discussed herein have a common structure and a common mode of operation. The common structure is a field-structured conducting composite comprising an (essentially) nonconducting medium containing a ordered aggregate structure of electrically conductive magnetic particles. These particles may simply be particles of magnetic material which intrinsically exhibit suitable electrical conductivity, or may be magnetic particles coated with a layer of conductive material. Other structures, such as clumps of magnetic particles sintered with a conducting binding material can also be used as electrically conductive magnetic particles.

The common mode of operation of the field-structured sensor devices disclosed here is that an environmental influence of interest, such as pressure or temperature or an absorbing solvent, is coupled by the structure of the device to a piece of field-structured conducting composite. When the environmental influence changes, so does the conductivity of the composite. This mode of operation applies whether the applied influence is stress, strain, temperature, magnetic field, electromagnetic radiation, or chemicals.

The sensor devices being claimed in the present application use a field-structured conductive composite. It is appropriate to briefly outline one way to reliably and reproducibly fabricate field-structured conducting composites.

A quantity of conducting magnetic particles is mixed into a polymerizable liquid which will remain liquid and at low viscosity until polymerization is initiated, by time, temperature, optical radiation, or other controllable process variable. A reasonable degree of uniformity in the mixture provides a useful initial state, but it not required for these applications. The volume fraction of conducting magnetic particles can vary widely, but is typically between 1% and 20%. A suitable size range for the conducting magnetic particles in a low-viscosity epoxy resin is 1–100$\mu$, although particles of nearly any size much smaller than the size of the desired piece of field-structured conducting composite can be used successfully. Iron, steel, and samarium cobalt particles were successfully used in a series of tests.

This initial mixture is then placed in a magnetic field. (For the materials described above, a field of several hundred Gauss is suitable, although much larger and smaller values can be used.) This magnetic field causes the conducting magnetic particles to aggregate the mixture in ordered formations. Development of the desired ordered aggregate structure can be monitored effectively by measuring the (typically anisotropic) bulk electrical conductivity of the evolving mixture. At this point, polymerization of the polymerizable liquid is initiated, and the conducting magnetic particles are immobilized in the solid polymer.

Having described the nature and fabrication of field-structured conductive composites, it remains only to describe how to couple environmental influences, to these materials to obtain sensor devices. The common structure among all these devices is a piece 200 of field-structured conducting composite mounted in such a manner that electrodes 201–202 or other means of measuring the bulk electrical conductivity of the piece of composite are in place. This canonical device is illustrated in FIG. 2.

Sensor devices of the present type can easily be made responsive to externally applied stresses and/or strains. Indeed, the simplest such device is simply the canonical device exposed to a gaseous or liquid atmosphere; the device will then produce a signal depending on the pressure of the gaseous or liquid surroundings. This is the essence of a barometer, a manometer, or a hydraulic pressure sensor.

Figure 2:
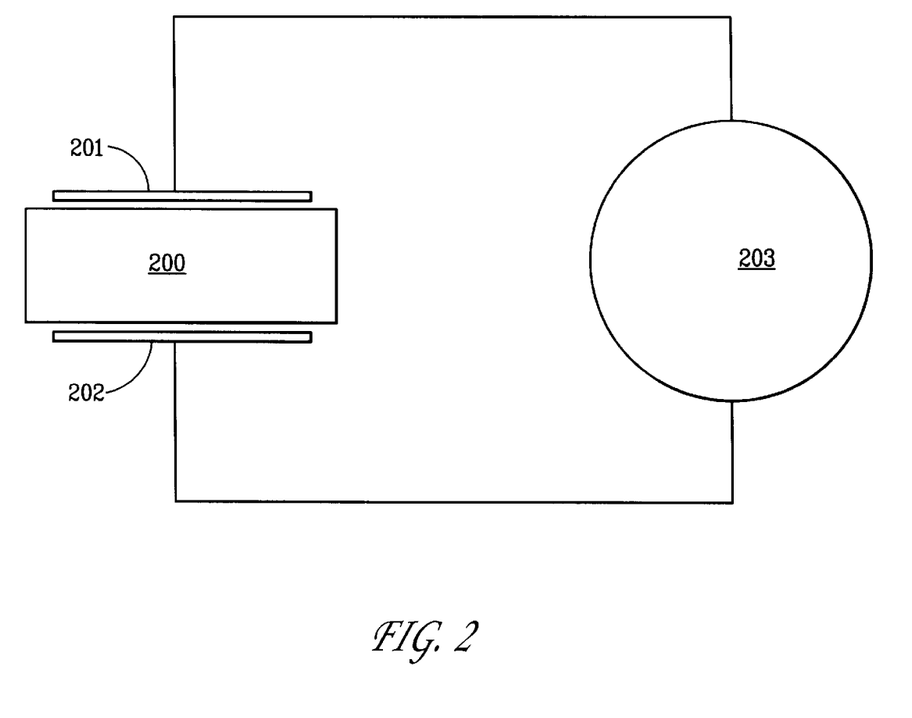
FIG. 2 shows a schematic illustration of a typical field-structured sensor device.
Figure 3A:
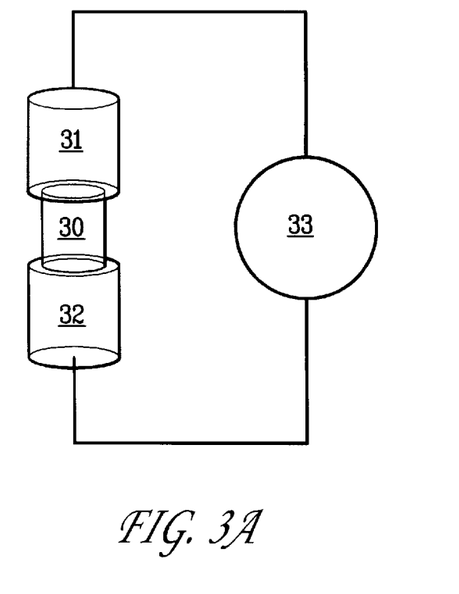
FIG. 3a shows a simple uniaxial stress sensor.

Modifications of the canonical device of FIG. 2 lead to numerous varieties of sensor devices. For example, FIG. 3 shows a series of sensor devices which measure an external applied stress. The stress is shown as uniaxial for simplicity, but need not be. FIG. 3a shows a slab 30 of field-structured conductive composite positioned between a pair of electrodes 31 and 32. The uniaxial stress is applied along the axes of electrodes 31 and 32 for simplicity only. A meter 33 or similar means allows measurement of the electrical conductivity of FSC slab 30. That conductivity is a function of the stress applied to the cylindrical electrodes.

Figure 3B:
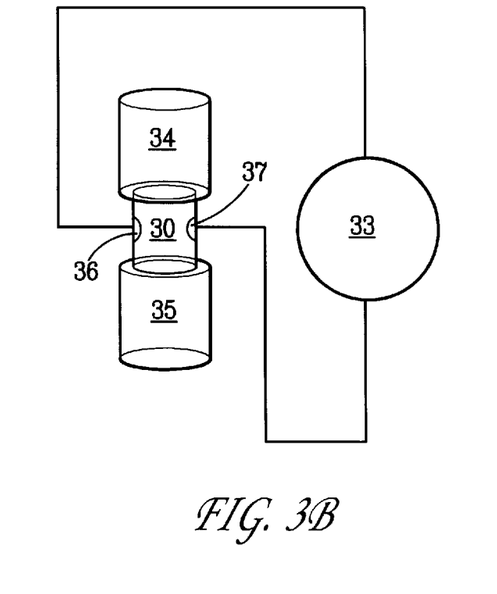
FIG. 3b shows another implementation of a uniaxial stress sensor.

FIG. 3b shows a modification of the above stress sensor. Here is found a similar FSC slab between two electrodes 34 and 35, but in this case the cylinders are not used to measure the conductivity of slab 30. Instead, a pair of electrodes 36 and 37 are mounted directly to the slab, and the conductivity of slab 30 is determined using a meter 33 or similar means applied across the electrodes.

Figure 3C:
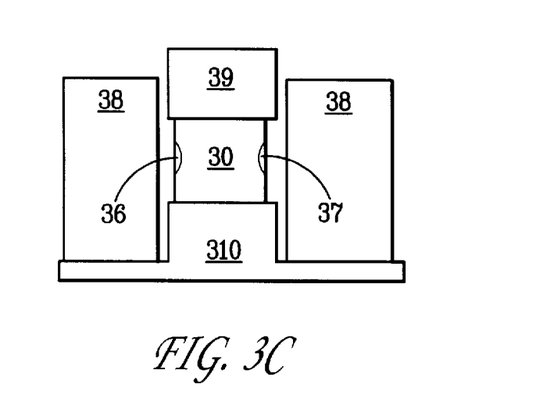
FIG. 3c shows a stress sensor with a stress isolation means.

A common feature in sensor devices based on the properties of FSC materials is the need to isolate the device against multiple inputs. For example, in the above devices slab 30 will not only change conductivity in response to applied stress, but also when the temperature changes, or possibly in the presence of certain chemicals, or in the presence of a magnetic field. Improved sensor performance often results when, as is shown in FIG. 3c, stress isolation means are added to the sensor device structure, in this case mounting to thermal insulation barrier 38, combined with insulating stress transfer dies 39 and 310.

The detailed nature of the isolation means will depend on the range of operating environments likely to be encountered. For example, in the case of the stress sensors described above, if the signal resulting from applied stress is similar to that expected from a 1° K change in temperature, stress isolation means are likely to be required, and would include means to prevent or compensate for even small temperature changes. Prevention could involve insulation or maintaining the FSC slab in a small oven, and compensation could involve measuring the temperature of the FSC slab (e.g., with a thermocouple) and correcting the conductivity measurement based on the known thermal coefficient of electrical conductivity of this well-characterized material.

Alternately, if the signal resulting from a 1° K change in temperature is 0.0001 of the likely stress-generated signal, any stress isolation means used would probably not require any accommodation for changes in temperature. Isolation means are designed to provide the required isolation for specific applications, and their exact structure will depend on the intended application. Many possibilities for suitable isolation means will be clear to a skilled worker for any environmental influence desired, and the current invention is not intended to be limited to those possibilities specifically called out.

Figure 4A:
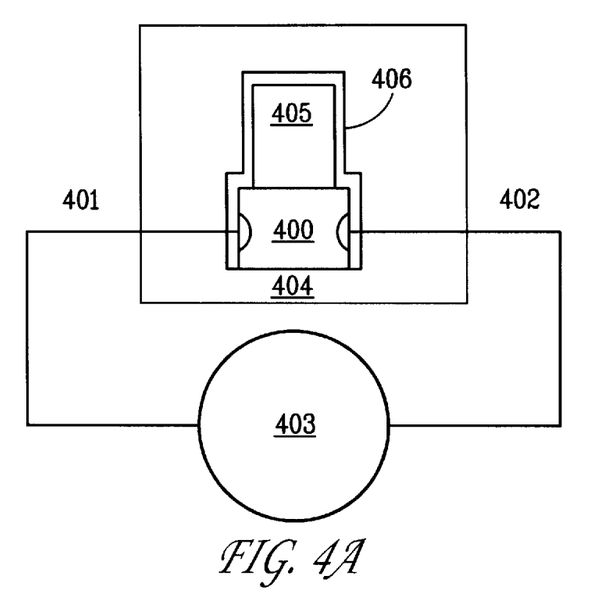
FIG. 4a shows a uniaxial acceleration sensor.
Figure 4B:
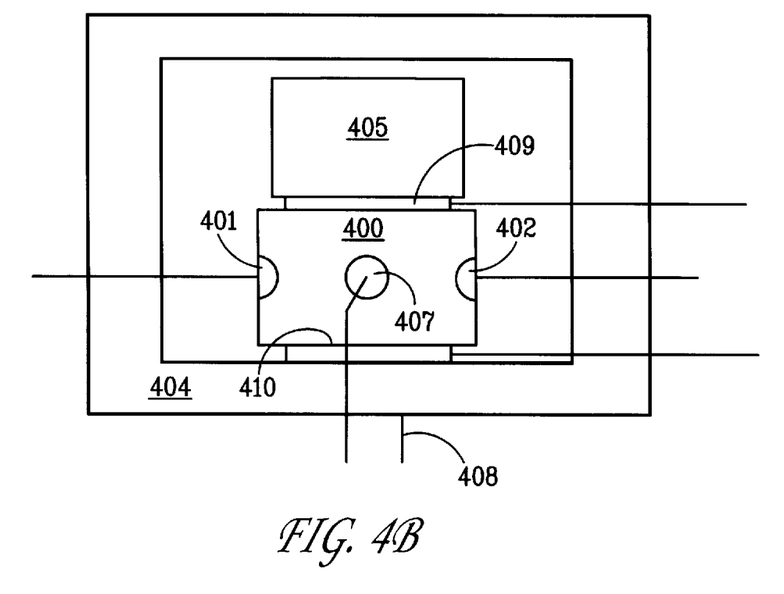
FIG. 4b shows a 3-axis acceleration sensor.

FIG. 4 shows a schematic design for an acceleration sensor. FIG. 4a shows a one-axis accelerometer, comprising a slab 400 of FSC material. Slab 400 has two electrodes 401 and 402, which are used along with meter 403 to measure the conductivity of the slab. The bottom surface of slab 400 is bonded or otherwise attached to the body 404 whose acceleration is to be measured, and the top surface of slab 400 is bonded or otherwise attached to the accelerometer mass 405. Motion guide 406 restricts the motion of mass 405 to take place along the desired axis. As the body is subjected to accelerations, the accelerometer mass responds in kind only when the slab transmits the body's accelerations to the mass. The conductivity of slab 400 will then be a known function of the body's acceleration.

In the above one-axis sensor, motion guide 406 was included so that the accelerometer mass 405 was only free to move along a single axis. This allowed the sensor to have a simple output. However, a multi-axis accelerometer can be made if this guide is eliminated, as in FIG. 4b, and a first, second, and third pair of electrodes 401–402, 407–408, and 409–410 are attached to FSC slab 400. The electrical conductance between each pair of electrodes is measured, and the accelerations along each axis are a complex but definable function of these three sets of conductivity measurements. The functional relation between these measured values and the accelerations is available for any specific accelerometer design through application of conventional constitutive modeling techniques.

The magnetic character of the ECMP in the field-structured conductive composite allows one to design another type of sensor —one that interacts with magnetic fields through the FSC medium. The generic response of an FSC medium to an external applied magnetic field will be an increase in the electrical conductivity of the medium. This results from the tendency of two magnetic particles in a field to coalesce.

The canonical device design of FIG. 2 can also be used as the basis for a thermometer. Here, the thermal expansion of the FSC material serves to slightly increase the distance between neighboring conducting particles, the result being a reduction in electrical conductivity with increasing temperature. As usual, thermal isolation means may be required for specific applications, although FSC materials tend to be more responsive to temperature change than most other influences.

Figure 5:
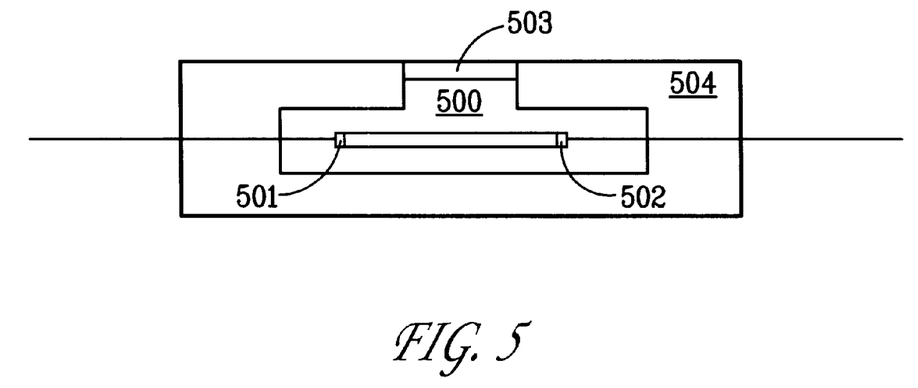
FIG. 5 shows a schematic illustration of a field-structured optical sensor.

The large responsivity of FSC materials to temperature change can be maximized by choosing the nonconducting medium to have a large coefficient of thermal expansion. If an FSC material also comprises material that efficiently absorbs electromagnetic radiation, a variation of the canonical sensor device as shown in FIG. 5 can be used as a bolometer whose purpose is sensing electromagnetic radiation. The main added feature is an optical access 503 such that electromagnetic radiation can be directed onto the FSC material. Such sensors can detect electromagnetic radiation ranging from mm-wave to ultraviolet radiation. Because of the extreme sensitivity of such devices to temperature changes, radiation isolation means (insulation, active temperature controls, etc.) are useful additions, indicated here as insulating case 504. Additionally, the use of contactless techniques for measuring the conductivity of FSC material 500 can help to provide the desired degree of thermal isolation.

Another approach to making a sensor for electromagnetic radiation has the same gross physical structure as shown in FIG. 5, but the FSC material has a different property. The bulk conductivity of an FSC material is dominated by the low conductivity of the medium in which the conducting particles are dispersed. If the conductivity of the medium increases slightly, the bulk conductivity of the FSC material also increases, usually in a nonlinear manner.

An example of a medium whose conductivity will change on exposure to electromagnetic radiation is a semiconductor. When exposed to electromagnetic radiation having energy larger than the semiconductor bandgap, electron-hole carrier pairs will be generated. These carriers move small distances within the semiconductor before recombining (especially if the semiconductor has an indirect bandgap), and their presence will dramatically alter the conductivity of the semiconductor medium.

Figure 6:
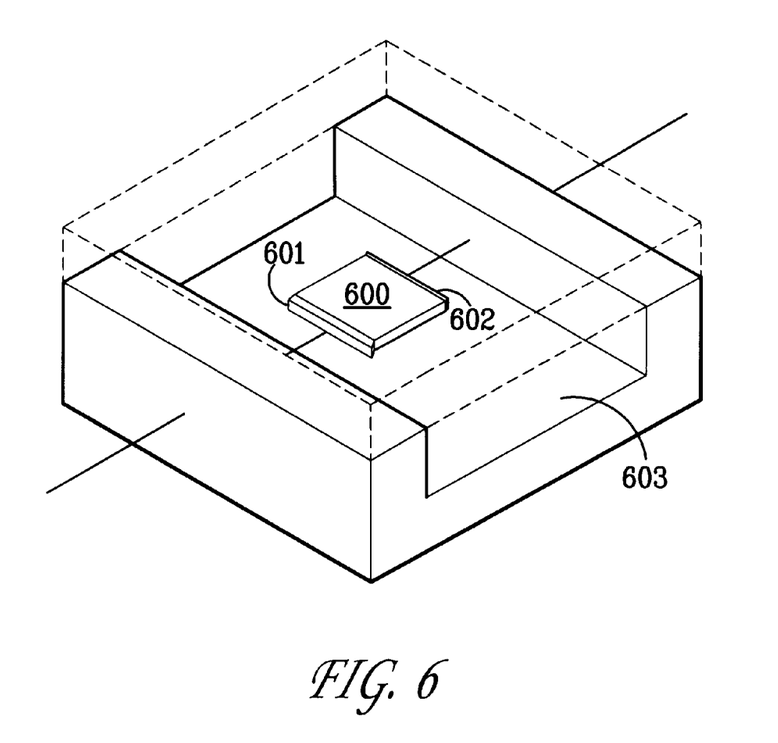
FIG. 6 shows a schematic illustration of a field-structured chemical sensor.

An additional implementation of the instant invention is capable of sensing specific classes of chemicals in the immediate environment of the sensor. As shown in FIG. 6, the conductivity of an FSC material 600 is monitored via electrodes 601 and 602. Director 603 directs environmental material onto the FSC material. This director is shown as a flow tube, but can take many forms which will be clear to the skilled worker. The FSC material for a chemically sensitive sensor will have a nonconducting medium whose conductivity changes in the presence of certain chemicals. In most cases, the sensitivity of the sensor will be greater if the FSC material 600 has a large surface to volume ratio, e.g., from roughening the surface, or by making the nonconducting material in the FSC material 600 porous.

The chemical in question can be water, for which two approaches toward FSC material design exist. In the first, the nonconductive medium absorbs the water and responds by expanding. Such behavior is characteristic of various gels. This increases the distance between the conducting particles, and thus reduces the bulk conductivity of the FSC material. In the second, the water dissolves, e.g., a salt comprising the FSC material. This creates mobile ions which carry current through the nonconductive medium, thus increasing the bulk conductivity of the FSC material.

In some cases, specific groups of environmental chemicals can be detected by field-structured sensor devices. For example, many polymers swell in volume when exposed to a variety of organic solvents. Ionic polymers can shrink or swell on exposure to polar and non-polar organics, respectively. It is possible to coat the surface of the (preferably porous) FSC material with a surfactant or other layer whose surface tension changes (which induces a change in the volume of the nonconducting medium) depending on the identify of any adsorbed or absorbed chemical species. Other configurations of FSC materials which result in bulk FSC conductivity depending on exposure to specific chemicals or related groups of chemicals will be clear to one skilled in the art.

Various implementations of the instant invention and applications thereof have been described in the proceeding. The extent of the invention is not intended to be limited to these implementations, however, but only by the appended claims.

What is claimed is:

1. A field-structured sensor to measure an environmental parameter, comprising:
   a) a field-structured composite comprising a solid nonconducting medium, and an ordered aggregate structure of conducting magnetic particles within said medium;
   b) electrodes positioned to allow the electrical resistance of said composite to be measured; and,
   c) a coupling mechanism which couples the environmental parameter to said composite.

2. The field-structured sensor of claim 1, further comprising environmental parameter isolation means such that the environmental parameter is the dominant influence affecting the electrical resistance of said composite.

3. The field-structured sensor of claim 2, wherein the environmental parameter isolation means comprise thermal insulation.

4. The field-structured sensor of claim 3, wherein the environmental parameter isolation means comprise a temperature controller.

5. The field-structured sensor of claim 2, wherein the environmental parameter isolation means comprise a chemical barrier.

6. The field-structured sensor of claim 2, wherein the environmental parameter isolation means comprise a substantially opaque barrier.

7. The field-structured sensor of claim 2, wherein the environmental parameter isolation means comprise a substantially rigid enclosure.

8. The field-structured sensor of claim 1, wherein the environmental parameter is stress applied to the sensor, and the coupling mechanism transmits stress applied to the sensor to said composite.

9. The field-structured sensor of claim 2, wherein the environmental parameter is stress applied to the sensor, and the coupling mechanism transmits stress applied to the sensor to said composite.

10. The field-structured sensor of claim 8, wherein the stress applied to the sensor is generated by an accelerometer mass in functional relation to the coupling mechanism.

11. The field-structured sensor of claim 10, wherein the electrodes are positioned so as to allow measurement of multiple axes of acceleration.

12. The field-structured sensor of claim 1, wherein the environmental parameter is an applied magnetic field.

13. The field-structured sensor of claim 2, wherein the environmental parameter is an applied magnetic field.

14. The field-structured sensor of claim 1, wherein the environmental parameter is temperature, and the coupling mechanism comprises a strong thermal link to the immediate environment of the sensor.

15. The field-structured sensor of claim 2, wherein the environmental parameter is temperature, and the coupling mechanism comprises a strong thermal link to the immediate environment of the sensor.

16. The field-structured sensor of claim 1, wherein the environmental parameter is electromagnetic radiation incident on the sensor, the coupling mechanism comprises optics which direct said electromagnetic radiation onto the field-structured composite, thereby heating the composite and changing its electrical conductivity.

17. The field-structured sensor of claim 2, wherein the environmental parameter is electromagnetic radiation incident on the sensor, and the coupling mechanism comprises optics which direct said electromagnetic radiation onto the field-structured composite, thereby heating the composite and changing its electrical conductivity.

18. The field-structured sensor of claim 1, wherein the environmental parameter is electromagnetic radiation incident on the sensor, the nonconducting medium is a semiconductor, the coupling mechanism comprises optics which direct said electromagnetic radiation onto the field-structured composite, generating electron-hole pairs within the nonconducting medium, thereby changing the electrical conductivity of the composite.

19. The field-structured sensor of claim 2, wherein the environmental parameter is electromagnetic radiation incident on the sensor, the nonconducting medium is a semiconductor, the coupling mechanism comprises optics which direct said electromagnetic radiation onto the field-structured composite, generating electron-hole pairs within the nonconducting medium, thereby changing the electrical conductivity of the composite.

20. The field-structured sensor of claim 1, wherein the environmental parameter is concentration of a selected chemical in a background carrier, and the coupling mechanism exposes the composite to said carrier.

21. The field-structured sensor of claim 20, wherein the nonconducting medium changes volume when exposed to the selected chemical.

22. The field-structured sensor of claim 20, wherein the surface stress of the nonconducting medium changes when exposed to the selected chemical.

23. The field-structured sensor of claim 20, wherein a surface of said composite is coated with a surface layer whose surface stress changes when exposed to the selected chemical.

24. The field-structured sensor of claim 20, wherein said nonconducting medium is porous.

25. The field-structured sensor of claim 2, wherein the environmental parameter is concentration of a selected chemical in a background carrier, and the coupling mechanism exposes the composite to said carrier.

* * * * *